United States Patent [19]
Klotz et al.

[11] Patent Number: 5,852,646
[45] Date of Patent: Dec. 22, 1998

[54] X-RAY IMAGING METHOD

[75] Inventors: Erhard P. A. Klotz, Neumünster; Reiner H. Koppe, Hamburg, both of Germany; John Op De Beek, Son; Hans Aerts, Berkel Enschot, both of Netherlands

[73] Assignee: U.S. Philips Corporation, New York, N.Y.

[21] Appl. No.: 852,301

[22] Filed: May 7, 1997

[30] Foreign Application Priority Data

May 21, 1996 [DE] Germany ............ 196 20 371.6

[51] Int. Cl.⁶ .................................................. A61B 6/03
[52] U.S. Cl. ........................ 378/8; 378/901; 382/130; 382/131
[58] Field of Search ........................ 378/8, 20, 41, 378/401; 382/130, 131

[56] References Cited

U.S. PATENT DOCUMENTS

| 4,418,387 | 11/1983 | Yamaguchi et al. | 378/11 |
| 4,422,146 | 12/1983 | Yamaguchi et al. | 378/22 |
| 5,493,595 | 2/1996 | Schoolman | 378/41 |
| 5,661,772 | 8/1997 | Bär et al. | 378/20 |
| 5,673,300 | 9/1997 | Reckwerdt et al. | 378/65 |

OTHER PUBLICATIONS

R. Koppe, E. Klotz, J. Op De Beek, H. Aerts, "3D Vessel Reconstruction Based on Rotational Angiography" Proceedings Car–95 Berlin, 1995, pp. 101–107.

Patrick J. Kelly, George J. Alker Jr., Bruce A. Kall, Stephan Goerss, "Method of Computed Tomography–Based Sterotactic Biopsy with Arteriographic Control", Neurosurgery, vol. 14, No. 2, 1984.

Primary Examiner—David P. Porta
Assistant Examiner—David Vernon Bruce
Attorney, Agent, or Firm—Dwight H. Renfrew, Jr.

[57] ABSTRACT

An X-ray imaging method, and device for carrying out the method, utilizes a first imaging device to form and digitally store a series of two-dimensional X-ray images in which an object to be examined is projected onto an X-ray image pick-up device from different perspectives, and a second imaging device to form a three-dimensional image of the same object. Quasi three-dimensional reproduction of anatomic structures is achieved by extracting a relevant structure of the object to be examined from the three-dimensional image, calculating synthetic, two-dimensional projection images of the extracted structure, the structure being projected with the same geometrical parameters as used for the relevant structure during the formation of the individual X-ray images, forming superposition images by superposing the synthetic projection images and the X-ray images formed under the same geometrical conditions, and displaying the series of superposition images.

9 Claims, 3 Drawing Sheets

X-RAY IMAGING METHOD

BACKGROUND OF THE INVENTION

1. Field of the Invention

The invention relates to an X-ray imaging method in which a series of two-dimensional X-ray images is formed and digitally stored by means of a first imaging device and in which the object to be examined is projected onto an X-ray image pick-up device from different perspectives. The invention also relates to a device for carrying out the method.

2. Description of the Related Art

A method and an arrangement of this kind are known from an article by Koppe et al in Proceedings CAR-95 Berlin, 1995, pp. 101–107, which will be referred to hereinafter as D1. This known method is preferably used for the imaging of the vascular system in which previously a contrast medium has been injected. Three-dimensional imaging of the vascular system would also be possible in principle, for example by means of MR or CT images. However, when such images are used, the vascular system cannot yet be reconstructed with the high spatial resolution required for various medical examinations. In the method described in the preamble, however, a high spatial resolution is obtained and a quasi three-dimensional spatial impression is obtained when the X-ray images are reproduced in rapid succession. It is a drawback, however, that the X-ray images then show only the vascular system whereas the tissue in the vicinity is not reproduced. For stereotactic examinations, however, it must be possible to determine the relative position of a structure of relevance to the examination, for example a tumor, with respect to the vascular system.

To this end, from a further publication (D2) by Kelly et al "in "Neurosurgery", vol. 14, No. 2, 1984, it is known to form, using an X-ray angiography device, on the one hand stereo image pairs which show the vascular system from the front and from the side, respectively, and on the other hand a three-dimensional image of the same region of the object to be examined by means of a computer tomograph. In order to link the findings in the two-dimensional X-ray images on the one hand and those in the three-dimensional CT image on the other hand, a reference frame is used, possibly in conjunction with reference marks, which is (are) reproduced in the X-ray images or the CT image in such a manner that the exact position of the anatomic structures to be examined can be determined in relation to the reference frame or the reference marks, and that findings from the various images can be correlated.

According to the known method the examiner defines a point in the three-dimensional CT image at which a biopsy is to be performed and a computer calculates on the basis thereof the mechanical settings of a stereotactic frame whereby the biopsy point can be moved to the focal point of the stereotactic frame. The horizontal and vertical angles at which a biopsy needle is introduced are determined on the basis of the angiographic X-ray images in which the points of vessels situated close to the path of the biopsy needle are digitized and entered into the computer which calculates the appropriate angle therefrom.

It is a drawback of this procedure that the examiner must rely on the calculations performed by the computer and is not given a direct, three-dimensional impression of the situation of the biopsy path in relation to the vascular system.

SUMMARY OF THE INVENTION

It is an object of the present invention to provide a method of the kind set forth in which the user is given an enhanced, quasi three-dimensional impression of the position of the structure of relevance to the diagnosis, for example a tumor, in relation to the anatomy reproduced in the X-ray images (for example, the vascular system). For example, in the case of a biopsy the examiner himself can then determine the optimum biopsy path or evaluate an automatically defined biopsy path.

This object is achieved by a method according to the invention which includes the following steps:

a) forming a three-dimensional image of the same object to be examined by means of a second imaging device b) extracting a relevant structure of the object to be examined from the three-dimensional image, c) calculating synthetic, two-dimensional projection images of the extracted structure, the structure being projected with the same geometrical parameters as used for the real structure during the formation of the individual X-ray images, d) forming superposition images by superposing the synthetic projection images and the X-ray images formed under the same geometrical conditions, e) displaying the series of superposition images.

Thus, according to the invention a synthetic, two-dimensional projection image is calculated for each X-ray image, which projection image represents the structure extracted from the three-dimensional image of a second imaging device (which may be a computer tomograph), that is to say with the same geometrical parameters as those with which the structure and, for example the vascular system are projected during the formation of the X-ray images. The structure is not visible in the X-ray images because of its low contrast; however, the contrast with which the structure is reproduced in the calculated synthetic projection image can be predetermined at will (reproduction in color is also possible). The corresponding X-ray image and the synthetic projection image are combined so as to form a superposition image and the superposition images are successively displayed as a series of images. The examiner is thus given a quasi three-dimensional impression of the examination zone in which the relative position of the extracted structure in relation to the anatomy reproduced in the X-ray images, for example the vascular system, can be recognized.

A preferred version of the invention utilizes an X-ray computer tomograph as the second imaging device which forms a number of computer tomograms of parallel slices so as to form a three-dimensional image of the object to be examined. However, it is in principle also possible to use a different modality for the formation of a three-dimensional image, for example an MR apparatus or an ultrasound apparatus.

In a further version of the invention, two series of images are displayed in order to form stereo image pairs, both series being derived from the series of superposition images and being offset a few superposition images relative to one another. If the image series are suitably displayed, the user is thus given a stereoscopic image impression for each individual superposition image, even though there is only a single image series. If the two superposition images which together constitute a stereo image pair are suitably chosen from the series (for example, in such a manner that they reproduce the object from perspectives offset 6° with respect to one another), a stereoscopic impression is created even though the two image series wherefrom the stereo image pairs are derived are not independent from one another but derived from the same series of superposition images. However, it is in principle also possible to form two separate image series which reproduce the examination zone with different projection geometries.

A preferred further version of the invention for the imaging of the vascular system of a patient involves the injection of a contrast medium injection, prior to the formation of the X-ray images, in order to form a series of X-ray images which reproduce the vascular system of the patient filled with contrast medium. This enables imaging of the vascular system. Such imaging of the vascular system can be further enhanced by forming a further series of X-ray images at a small distance in time from the one series of X-ray images, which further series reproduces the patient without contrast medium, the corresponding X-ray images of the two series being subtracted from one another in order to form difference images, the difference images and the synthetic projection images being superposed so as to form the superposition images.

An important condition to be satisfied by the superposition images for quantitative measurements is that these images correctly reproduce the anatomic structures supplied by the two imaging devices. However, if the X-ray image pick-up device of the first imaging device is an X-ray image intensifier, distortion of the X-ray images may occur due to the customary curvature of the entrance screen of the X-ray image intensifier as well as due to the terrestrial magnetic field. In a version of the invention these distortions are eliminated by a first correction step for the correction of the distortions due to the X-ray image pick-up device, which correction step applies a first set of stored correction parameters prior to the superposition step.

In an X-ray imaging system in which an X-ray source and the X-ray image pick-up device are attached to a C-arm, the X-ray images are also influenced by the fact that the C-arm is not rigid but is distorted under the influence of gravity and centrifugal forces, possibly also by mechanical oscillations. Consequently, the X-ray images are shifted or rotated relative to the ideal case (same relative position of the X-ray source in relation to the X-ray image pick-up device in all perspectives). This affects the accuracy of the superposition images. These adverse effects can be eliminated by means of a second correction step for the correction of the image transformations which are due to the changing of the relative position of the X-ray source with respect to the X-ray image pick-up device (image shift and image rotation), which second correction step applies a second set of stored correction parameters prior to the superposition step.

A device for carrying out the method according to the invention includes a first imaging device with an X-ray source and X-ray image pick-up device which are adjustable in relation to an object to be examined in order to form a series of two-dimensional X-ray images where the object to be examined is projected onto the X-ray image pick-up device from different perspectives, and also includes means for storing the X-ray images and programmable image processing means which are programmed so that the following image processing operations are performed:

b) extracting a relevant structure of the object to be examined from a three-dimensional image of the same object to be examined which has been formed by a second imaging device, c) calculating synthetic projection images of the extracted structure, the structure being projected with the same geometrical parameters as used for the real structure during the formation of the individual X-ray images, d) forming superposition images by superposing the synthetic projection images and the X-ray images formed under the same geometrical conditions, e) displaying the series of superposition images.

BRIEF DESCRIPTION OF THE DRAWING

The invention will be described in detail hereinafter with reference to the drawings. Therein.

DETAILED DESCRIPTION OF THE PREFERRED EMBODIMENTS

Figure 1:
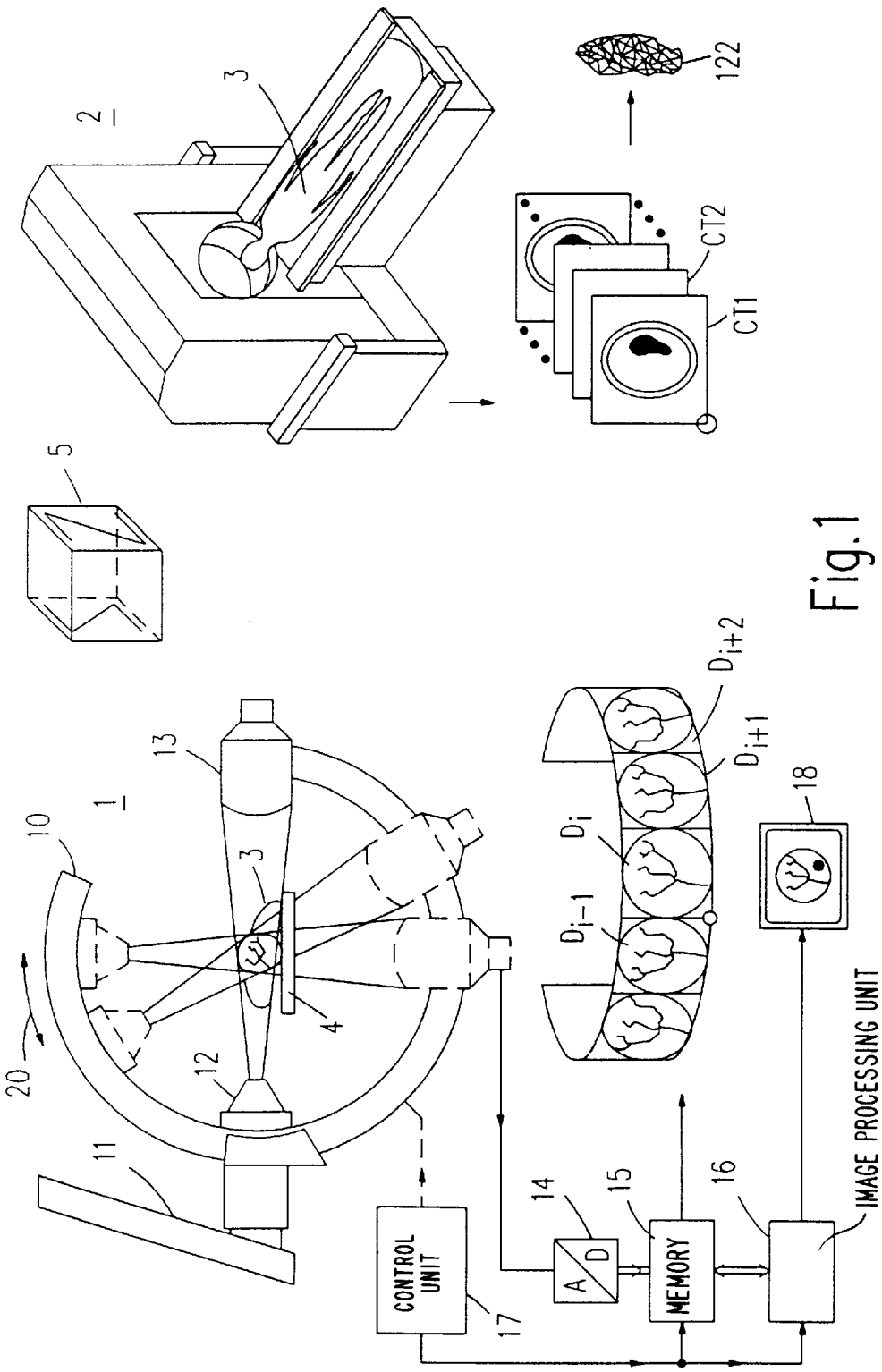
FIG. 1 shows diagrammatically a device which is suitable for carrying out the invention.

The reference numeral 1 in FIG. 1 denotes a first imaging device and the reference numeral 2 denotes a second imaging device. In order to relate the images of the first and the second imaging device, or the data derived from these images, to one another, use is made of a known reference frame 5 which is also imaged in the images of the two devices, possibly in conjunction with spherical reference marks. However, these images could in principle also be correlated on the basis of characteristic anatomic structures if detected by means of suitable image processing methods.

The first imaging device serves to form two-dimensional X-ray images of an object 3 to be examined, for example a patient, arranged on a table 4. The second imaging device serves to form a three-dimensional image. A "three-dimensional image" is to be understood to mean herein a data set which represents the absorption distribution in a three-dimensional zone in the object 3 to be examined and is derived from a number of two-dimensional computer tomograms CT1, CT2 . . . CTm of adjacently situated parallel slices of the object to be examined.

The first imaging device 1 includes a circular C-arm 10 which is mounted on a stand (11) which is only partly shown. The C-arm can be swivelled about a horizontal axis and be rotated through, for example 180° around its center in the direction of the double arrow 20 by means of a motor drive (not shown). The C-arm 10 accommodates an X-ray source 12 and an X-ray image pick-up device 13 which are aligned relative to one another in such a manner that an X-ray image can be formed of a volume to be examined around the said center point. A plurality of X-ray images can thus be formed, for example 100 images, which image the volume to be examined from different (reproducible) angular positions (some of which are denoted by dashed lines) of the image-forming system 12, 13.

The X-ray image pick-up device 13 may be an X-ray image intensifier whereto a television chain is connected whose output signals are digitized by an analog-to-digital converter 14 and stored in a memory 15 so that the overall X-ray image series will have been stored at the end of the examination. These X-ray images can be processed by an image processing unit 16. The images formed ( . . . $D_{i-1}$, $D_i$, $D_{i+1}$, $D_{i+2}$ . . . ) can be displayed on a monitor 18, either individually or as a series of images. The various components of the imaging system 1 are controlled by means of a control unit 17.

Figure 2:
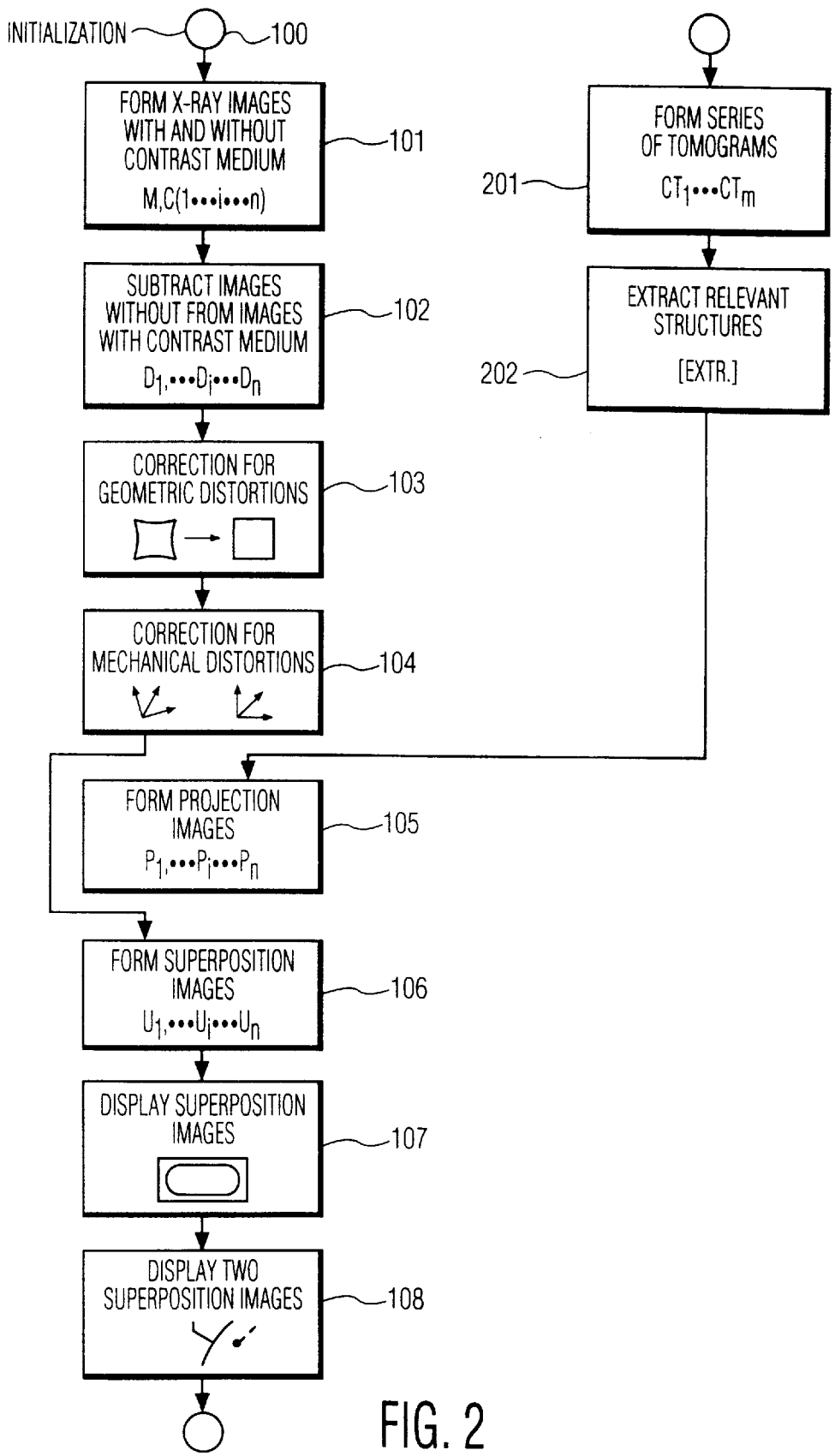
FIG. 2 illustrates the execution of the image processing operations.

FIG. 2 illustrates the series of steps for the two imaging systems. After initialization (100) of the first imaging system and injection of a contrast medium, a series of n X-ray images is formed (for example, n=100) which reproduce the object to be examined and the blood vessels which are present therein and filled with contrast medium (step 101). Before or after that a further series of X-ray images M is formed, which images reproduce the same object at the same perspectives as the X-ray images C, but do not show the vascular system (because either the contrast medium has not yet been injected or the contrast medium has already spread so far that it is no longer visible in the image).

Subsequently, the images M are subtracted (step 102) from the corresponding contrast images, formed in the same angular position, so that there is formed a series of difference images $D_1, \ldots D_i \ldots D_n$ which reproduce only the vascular system for the various angular positions, because the other anatomic structures have been eliminated by the subtraction. Instead of the difference images, however, it is also possible to use exclusively contrast medium images (without subtraction of images formed without contrast medium). In that case more contrast medium must be injected; however, bone structures can then be recognized still.

Before or after the formation of these X-ray images, a series of computer tomograms $C_1 \ldots C_n$ is made of the same anatomic region of the patient; this series represents the absorption distribution in neighboring parallel planes of the examination zone, resulting in a three-dimensional "image", i.e. a data set which characterizes the absorption distribution in a three-dimensional zone (step 201). In order to relate the image data derived from the various modalities 1 and 2 to one another, use is made of a reference frame, possibly in conjunction with reference marks, fixed relative to the region to be examined, for example the skull of the patient, and also imaged in the X-ray images or the computer tomograms. They can be detected in the X-ray images or the computer tomograms by means of automatic image processing methods and be used as a coordinate system so as to relate image data from one modality to image data from the other modality. This is described in detail in the document D2 whereto reference is explicitly made.

During the next step (202) a diagnostically relevant structure is extracted from the computer tomograms, for example a tumor or a given region in the brain (ventricle). This operation can be performed interactively by the user; however, automatic image processing methods which extract this structure by segmentation (202) are also feasible. Thus, not only the shape and the dimensions of the structure become known, but also its position in relation to a coordinate system associated with the reference window or the reference marks. In the simplest case it suffices to extract only a geometrical attribute from the structure, for example its center (center of gravity) or lines or simple geometrical bodies bounding this structure.

Before relating this structure to the X-ray images, it is often also necessary to correct or calibrate the X-ray images in order to take into account the real circumstances during the X-ray exposure. For example, geometrical distortions may occur if the X-ray image pick-up device includes an X-ray image intensifier which has a curved entrance screen and whose exit screen image may be influenced by the terrestrial magnetic field. In order to eliminate such distortions, in the step 103 the difference images $D_1 \ldots D_n$ are subjected to a geometrical transformation whose parameters have been determined and stored via a preceding calibration operation during which preferably a regular grid is arranged in the beam path and its reproduction in an X-ray image is evaluated. This is described in detail in the document D1 which is also explicitly referred to. If the X-ray image pick-up device does not induce such geometrical distortions, this step may be omitted.

Further factors which could influence the accuracy of the method according to the invention are due to the fact that the C-arm is not absolutely rigid. It is distorted under the influence of the force of gravity and centrifugal forces, so that the distance between the X-ray source and the image intensifier could change in dependence on the position of the C-arm in space. This distortion may also cause the isocenter (being situated on the central ray connecting the X-ray source to the center of the image pick-up device) whereto the coordinate system of relevance to the X-ray image is related is shifted and rotated from one X-ray image to another. The resultant changes in the X-ray images normally do not have a disturbing effect for as long as the X-ray images are observed individually. However, if image data of different X-ray images is to be related to one another or to image data of the CT image, the accuracy that can be achieved will suffer.

The correction of these effects, performed in the step 104, is based on the fact that the system 10, 11, 12, 13 (see FIG. 1) is reproducibly distorted during a rotation in the direction of the double arrow 20. The distortion can be determined by means of a calibration member during a preceding calibration method and the correction parameters which can be derived therefrom for each individual angular position are used for the correction of the X-ray images formed in these angular positions. This calibration and correction method is also described in detail in the document D1. It can be omitted if the C-arm is so rigid that the distortions cannot affect the X-ray images.

Figure 3:
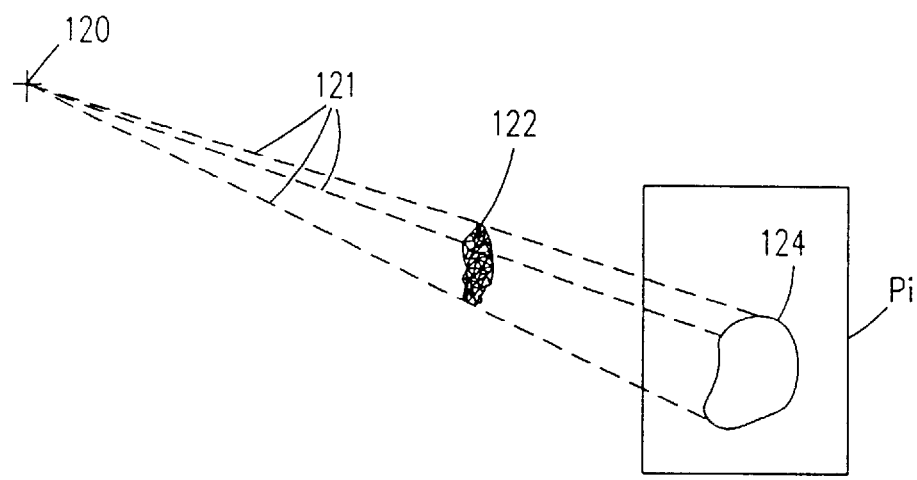
FIG. 3 shows the geometry underlying the calculation of the projection images.

During the next step (105) projection images of the extracted structure are formed, that is to say one for each difference image $D_1 \ldots D_i \ldots D_n$. FIG. 3 shows this operation for a single projection image, the projection center (corresponding to the X-ray source 12) being denoted by the reference numeral 120 whereas the projection rays emanating therefrom are denoted by the reference numeral 121 and the extracted structure by the reference numeral 122. The projection image (whose position corresponds to the X-ray image pick-up device 13) is denoted by the reference $P_i$. Such a projection image can be calculated in such a manner that it is determined whether at least one voxel of the extracted structure is present on a projection ray 121 leading to a pixel in the projection image $P_i$. If this is the case, a suitable image value is assigned to the pixel; if not, the image value 0 is assigned thereto. This is repeated for all pixels, thus yielding a projection image $P_i$ which represents a projection 124 of the structure. This operation is repeated for all angular positions of the system 12–13 in which X-ray images, or the difference images derived therefrom, were formed.

With each projection image $P_i$ thus formed there is associated an X-ray image, or a difference image $D_i$, the position of the projection center 120 and of the projection image $P_i$ in relation to the extracted structure 122 being determined by the position of the X-ray source, or of the X-ray image pick-up device, in relation to the real structure during the formation of the relevant X-ray image.

The synthetic projection images thus formed can represent the extracted structure with an arbitrary, selectable contrast but also in color. It is merely important to reproduce the anatomic details of the various images faithfully in respect of geometry but not in respect of contrast. Thus, during the projection step 105 a synthetic projection image is formed for each X-ray image, the projected structure in the projection image having the same shape and position as the real structure would have in the (possibly corrected) difference images $D_1 \ldots D_i \ldots D_n$ if it could be reproduced therein.

Figure 4:
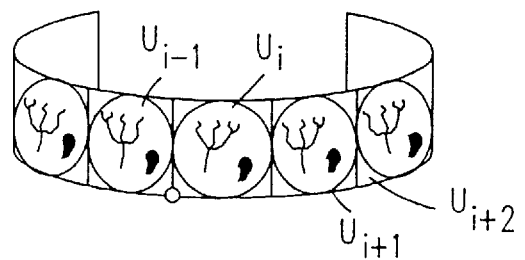
FIG. 4 shows a series of superposition images.

During the next step 106, the difference images $D_1 \ldots D_i \ldots D_n$, essentially showing the vascular system, and the synthetic projection images $P_1 \ldots P_i \ldots P_n$, representing the structure extracted from the CT image, are superposed, thus yielding a series of superposition images $U_1 \ldots U_i \ldots U_n$. (FIG. 4) which reproduces the two anatomic structures in geometrically correct association. This image series can be displayed on the monitor during the subsequent step 107, so that a quasi three-dimensional image impression is obtained which substantially facilitates the planning of a treatment, for example the presetting of a path for the introduction of a biopsy needle into the structure, or the evaluation of a previously calculated biopsy path. The biopsy path can be interactively fixed by means of a three-dimensional cursor. Distance measurements are possible by means of static image display (step 108) during which each time two superposition images (with different projection angles) are displayed. Volume measurements can also be performed. The execution of the method is then terminated.

According to the foregoing description first the synthetic projection images 105 were calculated and stored, after which the individual superposition images were formed. However, it is alternatively possible to calculate the associated synthetic projection image already during the display of an X-ray image or a difference image and to superpose the difference image and the projection image just calculated on the monitor 18, even if the X-ray images (or the difference images derived therefrom) are reproduced in comparatively rapid succession. Thus, it is not necessary to complete calculation of all synthetic projection images before superposing them on the difference images or X-ray images.

Also possible is stereoscopic observation where each time a stereo image pair is reproduced simultaneously for observation using the customary means. For this purpose it is not necessary to form separate X-ray images. It suffices to display each time two superposition images which reproduce the examination region from two angular positions which differ by approximately 6°, for example the superposition images $U_{i-1}$ and $U_{i+1}$ or the images $U_i$ and $U_{i+2}$ (see FIG. 4). Such stereoscopic reproduction facilitates not only the planning of a biopsy path but also the stereotactic measurements in the superposition images.

We claim:

1. An X-ray imaging method comprising forming and digitally storing a series of processed two-dimensional X-ray images of an object to be examined by use of a first imaging device, which projects radiation from an X-ray image through the object to be examined and onto an X-ray image pick-up device from different perspectives, forming a three-dimensional image of the same object to be examined by means of a second imaging device (2), extracting a relevant structure of the object to be examined from the three-dimensional image, calculating a series of synthetic, two-dimensional projection images of the extracted structure, the structure being projected with the same geometrical parameters as used for the same relevant structure during the formation of the individual X-ray images, forming a series of superposition images by superposing the synthetic projection images and the processed X-ray images formed from the same perspectives, and displaying the series of superposition images.

2. A method as claimed in claim 1, wherein an X-ray computer tomograph is used as the second imaging device, which forms a number of computer tomograms of parallel slices so as to form a three-dimensional image of the object to be examined.

3. A method as claimed in claim 1, wherein two processed series of images are displayed in order to form stereo image pairs, both series being derived from the series of superposition images and being offset a plurality of superposition images relative to one another.

4. A method as claimed in claim 1, wherein the object to be examined comprises a patient and wherein a contrast medium is injected into the vascular system of the patient prior to the formation of the processed series of X-ray images, in order to form a component series of X-ray images which reproduce the vascular system of the patient filled with contrast medium.

5. A method as claimed in claim 4, wherein a further component series of X-ray images is formed at a small distance in time from the other component series of X-ray images, which further component series reproduces the patient without contrast medium, said processed series of images being formed by subtracting corresponding X-ray images of the two component series from one another.

6. A method as claimed in claim 1, wherein said processed series of X-ray images are formed by a correction step for the correction of distortions due to the X-ray image pick-up device, which correction step applies a first set of stored correction parameters prior to forming the series of superposition images.

7. A method as claimed in claim 1, wherein said processed series of X-ray images are formed by a correction step for the correction of image transformations which are due to changing the relative position of the X-ray source with respect to the X-ray image pick-up device, which correction step applies a set of stored correction parameters prior to forming the series of superposition images.

8. An X-ray image processing device comprising a first imaging device with an X-ray source and an X-ray image pick-up device which are adjustable in relation to an object to be examined in order to form a series of two-dimensional X-ray images where the object to be examined is projected onto the image pick-up device from different perspectives, and also including means for storing the X-ray images and programmable image processing means which are programmed so that the following image processing operations are performed:

b) extracting a relevant structure of the object to be examined from a three-dimensional image of the same object to be examined which has been formed by a second imaging device, c) calculating synthetic projection images of the extracted structure, the structure being projected with the same geometrical parameters as used for the relevant structure during the formation of the individual X-ray images, d) forming superposition images by superposing the synthetic projection images and the X-ray images formed from the same perspectives, and e) displaying the series of superposition images.

9. A device as claimed in claim 8, wherein the first imaging device comprises a C-arm whereto the X-ray source and the X-ray image pick-up device are attached, which C-arm can be moved to a plurality of exposure positions along a circular path.

* * * * *